United States Patent [19]

Yagihara et al.

[11] Patent Number: 4,978,385
[45] Date of Patent: Dec. 18, 1990

[54] 4-HALOPYRIDINE-3-CARBOXAMIDE COMPOUNDS AND HERBICIDAL COMPOSITIONS THEREOF

[75] Inventors: Hiroshi Yagihara; Yukihisa Goto, both of Himeji; Kazuhisa Masamoto, Arai; Yasuo Morishima, Kobe; Hirokazu Osabe, Himeji, all of Japan

[73] Assignee: Daicel Chemical Industries Ltd., Japan

[21] Appl. No.: 199,187

[22] Filed: May 26, 1988

[30] Foreign Application Priority Data

May 29, 1987 [JP] Japan ............................ 62-131696
Oct. 16, 1987 [JP] Japan ............................ 62-262333

[51] Int. Cl.$^5$ ................ A01N 43/40; A01N 43/42; C07D 221/02; C07D 215/38
[52] U.S. Cl. ..................................... 71/94; 546/112; 546/169; 546/291; 546/316; 546/274; 546/275; 546/269; 546/279; 546/280; 546/283; 546/284; 544/238; 544/284; 544/333; 544/353; 544/405; 71/92
[58] Field of Search ............... 71/94; 546/291, 316, 546/169, 112

[56] References Cited

U.S. PATENT DOCUMENTS 4,001,416  1/1977  Pommer et al. ............... 546/316
4,312,870  1/1982  Yokohama ..................... 546/316

FOREIGN PATENT DOCUMENTS 53462   3/1982  Japan ........................ 546/316
29764   2/1983  Japan ........................ 546/316
112967  6/1984  Japan ........................ 546/316

OTHER PUBLICATIONS

Chemical Abstracts, 88: 6686s (1978).
Chemical Abstracts, 83: 58620g (1975).
Chemical Absrtacts: 55: 11413g (1961).

Primary Examiner—Mary C. Lee
Assistant Examiner—J. Richter
Attorney, Agent, or Firm—Bryan, Cave, McPheeters & McRoberts

[57] ABSTRACT

A compound of the formular (I)

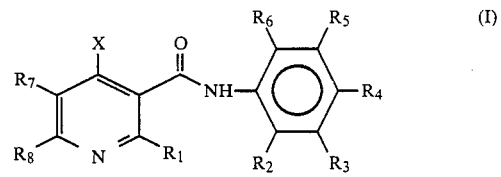

or 1-oxide or salt thereof, wherein $R_1$ is a $C_{1-11}$ alkyl group, a lower alkenyl group, a phenyl or group which may be substituted, an aralkyl group whose nucleus may be substituted, a haloalkyl or a 5- or 6-membered heterocycle group;

$R_2$, $R_3$, $R_4$, $R_5$ and $R_6$ are, the same or different, hydrogen atom, a halogen atom, cyano group, nitro group, amino group, a lower alkyl group, a lower haloalkyl group, hydroxy group, a lower alkoxy group, an aryloxy group, carboxy group or a lower alkoxycarbonyl group;

$R_7$ is hydrogen atom, a halogen atom, a lower alkyl group, a phenyl group which may be substituted, an aralkyl group whose nucleus may be substituted, a lower alkenyl group, a lower alkynyl group, a lower alkoxy group or a haloalkyl group;

$R_8$ is a $C_{1-11}$ alkyl group, a lower alkenyl group, a lower alkynyl group, a cycloalkyl group, a lower alkoxyalkyl group, a lower alkylthioalkyl group, a phenyl group which may be substituted, an aralkyl group whose nucleus may be substituted, a haloalkyl group or a 5 or 6 membered heterocycle group; or $R_7$ and $R_8$ may be combined to form a group of —(CH$_2$)$_m$— (m is 3 or 4); X is a halogen atom, which can be used as herbicidal compositions.

30 Claims, No Drawings

4-HALOPYRIDINE-3-CARBOXAMIDE COMPOUNDS AND HERBICIDAL COMPOSITIONS THEREOF

BACKGROUND OF THE INVENTION

1. Field of the Invention

This invention relates to novel 4-halopyridine-3-carboxamide compounds and herbicidal composition thereof.

2. Description of the Prior Arts

Certain 4-halopyridine compounds 4-halopyridinecarboxamide are disclosed in the literature.

That is, German Laid-open Patent Application No. 2417216 discloses 4-chloro-N-phenyl-3-pyridinecarboxamide hydrochloride as a bactericidal agent. Bala, Marian et al. (Chem. Abst., 88, 6686s) reported 4-chloro-N, 2-diphenyl-3-quinolinecarboxamide, 4-chloro-N-methyl-N, 2-diphenyl-3-quinolinecarboxamide, 4-chloro-N-(4-methylphenyl)-2-phenyl-3-quinolinecarboxamide, 4-chloro-N-(4-methoxyphenyl)-2-phenyl-3-quinolinecarboxamide and 4-chloro-N-(4-N',N'-dimethylaminophenyl)-2-phenyl-3-quinolinecarboxamide which were prepared by the reaction of quinoline-3-carbonylchloride compounds with amines, and each structure was confirmed with an ultraviolet and an infrared spectrum thereof. 4-Chloro-N, 2-diphenyl-3-quinolinecarboxamide was also obtained by a method similar to that disclosed by Bala, Marian et al. (Zankowska-Jasinsca, Wanda et al, Chem. Abst., 83, 58620 g). Nagano (Chem. Abst., 55, 11413 g) reported the preparation of 4-chloro-N-phenyl-3-quinolinecarboxamide, 4-chloro-N-(4-ethoxyphenyl)-3-quinolinecarboxamide and 4-chloro-N-(4-methoxyphenyl)-3-quinolinecarboxamide by treating the corresponding 4-hydroxy compounds with phosphorus oxychloride. U.S. Pat. No. 4,312,870 and European Patent Application No. 168350 described 4-chloro-N-(4-chlorophenyl)-3-quinolinecarboxamide and 4-chloro-N-(4-chlorophenyl)-5,6,7,8-tetrahydro-3-quinolinecarboxamide as the raw materials for pyrazoloquinoline compounds having attractic activity. Japanese Unexamined Patent Publication Nos. 59(1984)-112967, 58(1983)-29764 and 57(1982)-53462 disclosed certain 3-carbamoylpyridine derivatives possessing herbicidal effect. However, all the compounds disclosed in the above mentioned 59(1984)-112967 and 58(1983)-29764 publications have an N-benzylcarbamoyl group at the 3rd position of the pyridine ring, while those disclosed in the above mentioned 57(1982)-53462 publications are N-phenyl-3-pyridinecarboxamide derivatives in which however the 4th position of the pyridine ring is a hydrogen atom and the 5th position is substituted by cyano, carboxyl or a lower alkoxycarbonyl. Therefore, the compounds disclosed in the above mentioned three Japanese patent publications are structurally different from the compounds of the formula (I) as mentioned below.

As discussed above, there were no reports on the 4-halopyridine-3-carboxamide compounds of formula (I), nor any suggestion on their herbicidal activities.

SUMMARY OF THE INVENTION

This invention provides 4-halo-3-pyridinecarboxamide compounds of the formula (I):

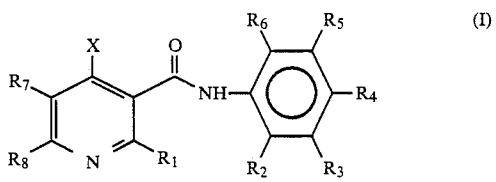

or the 1-oxide or a salt thereof,
wherein $R_1$ is a $C_{1-11}$ alkyl group, a lower alkenyl group, a lower alkynyl group, a cycloalkyl group, a lower alkoxyalkyl group, a lower alkylthioalkyl group, a phenyl group which may be substituted, an aralkyl group whose nucleus may be substituted, a haloalkyl group or a 5- or 6-membered heterocycle group;

$R_2$, $R_3$, $R_4$, $R_5$ and $R_6$ are the same or different and can be a hydrogen atom, a halogen atom, a cyano group, a nitro group, an amino group, a lower alkyl group, a lower haloalkyl group, a hydroxy group, a lower alkoxy group, an aryloxy group, a carboxy group or a lower alkoxycarbonyl group;

$R_7$ is a hydrogen atom, a halogen atom, a lower alkyl group, a phenyl group which may be substituted, an aralkyl group whose nucleus may be substituted, a lower alkenyl group, a lower alkynyl group, a lower alkoxy group or a haloalkyl group;

$R_8$ is a $C_{1-11}$ alkyl group, a lower alkenyl group, a lower alkynyl group, a cycloalkyl group, a lower alkoxyalkyl group, a lower alkylthioalkyl, a phenyl group which may be substituted, an aralkyl group whose nuleus may be substituted, a haloalkyl group or a 5- or 6-membered heterocycle group; or $R_7$ and $R_8$ may be combined to form a group of $-(CH_2)_m-$ (m is 3 or 4); and X is a halogen atom;
and the 1-oxide or salt thereof.

The term "lower" used for the lower alkyl, lower alkoxy or like group in this invention means a group containing 1-5 carbon atoms. Specifically, the lower alkyl group may be methyl, ethyl, propyl, isopropyl, butyl, isobutyl, pentyl or isopentyl; the lower alkoxy group may be methoxy, ethoxy, propoxy, isopropoxy or butoxy; the lower alkoxycarbonyl group may be methoxycarbonyl, ethoxycarbonyl, propoxycarbonyl or butoxycarbonyl; and the lower alkylthio group may be methylthio, ethylthio, propylthio, isopropylthio, butylthio, pentylthio.

Also, the term "lower" used for the lower alkenyl or lower alkynyl group in this invention means a group containing 2-6 carbon atoms. Specifically, the lower alkenyl or lower alkynyl group may be vinyl, allyl, 1-propenyl, isopropenyl, 2-butenyl, 3-butenyl, 2-methyl-2-propenyl, 3-methyl-2-butenyl, 1,3-butadienyl, 2-pentenyl, 1,4-pentadienyl, 1,6-heptadienyl, 1-hexenyl, ethynyl or 2-propynyl.

Examples of the $C_{1-11}$ alkyl groups include those specifically mentioned in the lower alkyl groups and also hexyl, heptyl, octyl, nonyl, decyl and undecyl.

The cycloalkyl groups include cycloalkyl having 3 to 6 carbon atoms such as cyclopropyl, cyclopentyl or cyclohexyl.

Examples of the haloalkyl groups include trifluoromethyl, difluoromethyl, chloromethyl, 2,2,2-trifluoroethyl or 3-chloropropyl.

Examples of the lower alkoxyalkyl groups include methoxymethyl, methoxyethyl, ethoxymethyl, propoxymethyl or butoxymethyl.

Examples of the halogen atoms include chlorine, bromine, fluorine or iodine.

Examples of the aralkyl in the aralkyl group whose nucleus may be substituted include benzyl, phenethyl, 3-phenylpropyl, 4-phenylbutyl.

The phenyl in these aralkyl groups whose nucleus may be substituted may be substituted by one or two groups selected from the above mentioned halogen atom, lower alkyl groups and lower alkoxy group.

Similarly, the phenyl in the phenyl which may be substituted may be substituted by one or two groups as mentioned above.

Examples of the aryloxy groups include phenyloxy or naphthyloxy.

The 5- or 6-membered heterocycle group means a 5- or 6-membered ring containing one to three hetero atoms selected from a nitrogen atom, an oxygen atom and a sulfur atom. Examples of the 5-membered heterocycle groups are furyl, tetrahydrofuryl, thienyl, thiazolyl, isothiazolyl, oxazolyl, isoxazolyl or pyrazolyl and the 6-membered heterocyclic groups are pyridyl, pyrimidinyl, pyrazinyl or pyridazinyl. These heterocycle groups may be substituted by an alkyl as methyl or ethyl, a halogen atom or phenyl. Further, the heterocyclic group may form a condensed ring combining the two adjacent carbon atoms in the heterocycle group with a benzene. Examples of the condensed rings include benzothiazolyl, benzofuryl, quinazolinyl or quinoxalinyl group.

The compounds (I) of this invention are useful as herbicides for paddy fields, vegetable field (fields farm), fruit gardens, meadows, lawns, woods and other fields of grass.

For herbicidal applications, the compounds of the present invention may be used as they are, but are generally formulated into herbicidal compositions such as wettable powders, granules or emulsifiable concentrates, in admixture with solid carriers, liquid carriers, surfactants and/or other adjuvants for preparations.

These compositions may preferably contain 10-80% for wettable powders, 0.1-20% for granules, or 10-50% for emulsifiable concentrates by weight of the active compound of this invention.

Examples of the solid carriers to be used for the compositions include fine powders or granules such as kaolinites, bentonites, clays, talcs, silicas, zeolite, pyrophilites, synthetic oxygen-containing silicones or calcium carbonate. Examples of the liquid carriers include aromatic hydrocarbons such as xylene or methylnaphthalene; alcohols such as ethanol, isopropanol, ethylene glycol or methylcellusolve; ketones such as acetone, isophorore or cyclohexanone; vegetable oils such as soya bean oil or cotton oil; or dimethylformamide, diemthylsulfoxide, acetonitrile or water.

Surfactants for dispersing or emulsifying are generally used with the liquid compositions. Their examples include nonionic types such as polyoxyethylene alkyl ethers, polyoxyethylene alkylaryl ethers, polyopxyethylene fatty acid esters sorbitan fatty acid esters, polyoxyethylene sorbitan fatty acid esters or polyoxyethylene polyoxypropylene blockpolymer; or anionic types such as alkylsulfonates, alkylaryl sulfonates or polyoxyethylene alkylsulfates.

Examples of the adjuvants include lignine sulfates, arginates, polyacrylates, polyvinyl alcohol, vegetable gums, carboxymethylcellulose (CMC) or hydroxyethylcellulose (HEC).

Also, the compounds of this invention can be, when needed, used in admixutre with insecticides, acaricides, nematicides, bactericides, other herbicides, plant growth regulators, fertilizers or soil conditioners.

Dosage of the herbicidal compositions is generally 0.1-50 g by weight of the active compound, per acre, although it varies depending upon places, method of application and kinds of plants.

The compounds of the formula (I) in this invention may be prepared by any of the following methods.

METHOD A

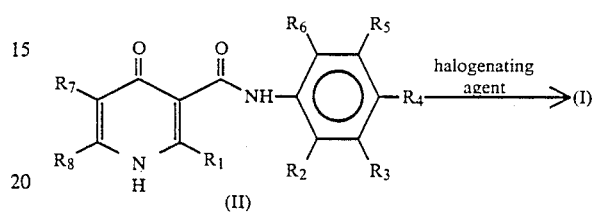

wherein $R_1$, $R_2$, $R_3$, $R_4$, $R_5$, $R_6$, $R_7$ and $R_8$ of the formula (II) are the same as those in the formula [I].

This method comprises reacting a 1,4-dihydro-4-oxo-3-pyridine carboxamide compound of the general formula (II) with a halogenating agent in the presence or absence of an appropriate solvent (e.g., toluene, benzene or mesitylene) while heating (e.g., at 50°-200° C.). The halogenating agent includes phosphorus oxychloride, phosphorus pentachloride, phosphorus oxybromide, phosphorus pentabromide, or phosphorus tribromide. This method is suitable to obtain a compound of the formula (I), wherein X is a bromine or chlorine atom.

METHOD B

This method is a halogen-exchange reaction and comprises reacting a compound of the general formula (I) with an alkali halide, transition metal halide or metal halide in the presence or absence of an appropriate solvent (e.g., acetone, 2-butanone, N,N-dimethylformamide, dimethylsulfoxide, sulfolane or benzonitrile) at a temperature of over room temperature to the reflux temperature of the solvent to be used and, if necessary, under pressure. This method may be used to obtain especially a compound of formula (I) wherein X is fluorine or iodine.

METHOD C

The 1-oxide compounds may be prepared by reacting a pyridine compound of the formula (I) with a peroxide (e.g., m-chloroperbenzoic acid, hydrogen peroxide or peracetic acid) in an appropriate solvent (e.g., chloroform or methylene chloride).

The compounds of the formula (I) or 1-oxides thereof may form the corresponding salts with inorganic acids such as hydrochloric acid, sulfuric acid or phosphoric acid, or organic acids such as methanesulfonic acid, p-toluenesulfonic acid, trifluoroacetic acid, succinic acid, oxalic acid or tartaric acid. Also, they may form the corresponding pyridinium salts with halogen compounds such as methyl iodide, or sulfonates such as methyl methanesulfonate. Further, in the case where $R_2$, $R_3$, $R_4$, $R_5$ or $R_6$ in the formula (I) is a carboxyl, the carboxyl group may form the salt with a base such as sodium hydroxide, potassium hydroxide, calcium hydroxide, triethylamine or ethanolamine. The formation of such salts as mentioned can be conducted in accordance with a conventional method. It should be understood that the salts as mentioned above are included in the invention.

Furthermore, compounds of interest in addition to the compounds shown in the examples are as follows;

4-bromo-N-(2,6-diethylphenyl -2,5,6-trimethyl-3-pyridinecarboxamide,
4-bromo-5-ethyl-N-(2,6-diethylphenyl)-2,6-dimethyl-3-pyridinecarboxamide,
4-bromo-N-(2,6-diethylphenyl)-2,6-dimethyl-5-propyl-3-pyridinecarboxamide,
4-bromo-5-butyl-N-(2,6-diethylphenyl)-2,6-dimethyl-3-pyridinecarboxamide,
4-bromo-N-(2,6-diethylphenyl)-2,6-dimethyl-5-(2-methylpropyl)-3-pyridinecarboxamide,
4-bromo-N-(2,6-diethylphenyl)-2,6-dimethyl-5-pentyl-3-pyridinecarboxamide,
4-bromo-N-(2,6-diethylphenyl)-2,6-dimethyl-5-(3-methylbutyl)-3-pyridinecarboxamide,
4-bromo-N-(4-bromo-2,6-diethylphenyl)-2,5,6-trimethyl-3-pyridinecarboxamide,
4-bromo-N-(4-bromo-2,6-diethylphenyl)-5-ethyl-2,6-dimethyl-3-pyridinecarboxamide,
4-bromo-N-(4-bromo-2,6-diethylphenyl)-2,6-dimethyl-5-propyl-3-pyridinecarboxamide,
4-bromo-N-(4-bromo-2,6-diethylphenyl)-5-butyl-2,6-dimethyl-3-pyridinecarboxamide,
4-bromo-N-(4-bromo-2,6-diethylphenyl)-2,6-dimethyl-5-(2-methylpropyl)-3-pyridinecarboxamide,
4-bromo-N-(4-bromo-2,6-diethylphenyl)-2,6-dimethyl-5-pentyl-3-pyridinecarboxamide,
4-bromo-N-(4-bromo-2,6-diethylphenyl)-2,6-dimethyl-5-(3-methylbutyl)-3-pyridinecarboxamide,
N-(2,6-diethylphenyl)-4-iodo-2,5,6-trimethyl-3-pyridinecarboxamide,
5-ethyl-N-(2,6-diethylphenyl)-4-iodo-2,6-dimethyl-3pyridinecarboxamide,
N-(2,6-diethylphenyl)-4-iodo-2,6-dimethyl-5-propyl-3-pyridinecarboxamide,
5-butyl-N-(2,6-diethylphenyl)-4-iodo-2,6-dimethyl-3-pyridinecarboxamide,
N-(2,6-diethylphenyl)-4-iodo-2,6-dimethyl-2-(2-methylpropyl)-3-pyridinecarboxamide,
N-(4-bromo-2,6-diethylphenyl)-5-ethyl-4-iodo-2,6-dimethyl-3-pyridinecarboxamide,
N-(4-bromo-2,6-diethylphenyl]-4-iodo-2,6-dimethyl-5-propyl-3-pyridinecarboxamide,
N-(4-bromo-2,6-diethylphenyl)-5-butyl-4-iodo-2,6-dimethyl-3-pyridinecarboxamide,
N-(4-bromo-2,6-diethylphenyl)-4-iodo-2,6-dimethyl-5-(2-methylpropyl)-3-pyridinecarboxamide,
5-ethyl-N-(2,6-diethylphenyl)-4-fluoro-2,6-dimethyl-3-pyridinecarboxamide,
N-(2,6-diethylphenyl)-4-fluoro-2,6-dimethyl-5-propyl-3-pyridinecarboxamide,
5-butyl-N-(2,6-diethylphenyl)-4-fluoro-2,6-dimethyl-3-pyridinecarboxamide,
N-(2,6-diethylphenyl)-4-fluoro-2,6-dimethyl-5-(2-methylpropyl)-3-pyridinecarboxamide,
N-(4-bromo-2,6-diethylphenyl)-5-ethyl-4-fluoro-2,6-dimethyl-3-pyridinecarboxamide,
N-(4-bromo-2,6-diethylphenyl)-4-fluoro-2,6-dimethyl-5-propyl-3-pyridinecarboxamide,
N-(4-bromo-2,6-diethylphenyl)-5-butyl-4-fluoro-2,6-dimethyl-3-pyridinecarboxamide,
N-(4-bromo-2,6-diethylphenyl)-4-fluoro-2,6-dimethyl-5-(2-methylpropyl)-3-pyridinecarboxamide,
N-(4-bromo-2,6-diethylphenyl)-4-chloro-2,6-diethyl-5-(2-propynyl)-3-pyridinecarboxamide,
4-chloro-N-(2,6-diethyl-4-methoxyphenyl)-2,6-dimethyl-5-(2-propynyl)-3-pyridinecarboxamide,
4-chloro-N-(2,6-diethyl-4-methylphenyl)-2,6-dimethyl-5-(2-propynyl)-3-pyridinecarboxamide,
4-chloro-N-(2,6-diethyl-4-iodophenyl)-2,6-dimethyl-5-(2-propynyl)-3-pyridinecarboxamide,
4-chloro-N-(2,6-diethyl-4-fluorophenyl)-2,6-dimethyl-5-(2-propynyl)-3-pyridinecarboxamide,
4-chloro-N-(3-bromo-4-methyl-2,6-diethylphenyl)-2,6-dimethyl-5-(2-propynyl)-3-pyridinecarboxamide,
5-allyl-N-(3-bromo-4-methyl-2,6-diethylphenyl)-4-chloro-2,6-dimethyl-3-pyridinecarboxamide,
5-(2-butenyl)-4-chloro-N-(4-chloro-2,6-diethylphenyl)-2,6-dimethyl-3-pyridinecarboxamide,
5-(2-butenyl)-N-(4-bromo-2,6-diethylphenyl)-4-chloro-2,6-dimethyl-3-pyridinecarboxamide,
5-(2-butenyl)-4-chloro-N-(2,6-diethyl-4-methylphenyl)-2,6-dimethyl-3-pyridinecarboxamide,
5-(2-butenyl)-4-chloro-N-(2,6-diethyl-4-methoxyphenyl)-2,6-dimethyl-3-pyridinecarboxamide,
5-(2-butenyl)-4-chloro-N-(2,6-diethyl-4-fluorophenyl)-2,6-dimethyl-3-pyridinecarboxamide,
N-(3-bromo-2,6-diethyl-4-methylphenyl)-5-(2-butenyl)-4-chloro-2,6-dimethyl-3-pyridinecarboxamide,
5-(2-butenyl)-4-chloro-N-(2,6-diethyl-4-iodophenyl)-2,6-dimethyl-3-pyridinecarboxamide,
4-chloro-N-(2,6-diethylphenyl)-5-methoxy-2,6-dimethyl-3-pyridinecarboxamide,
4-chloro-N-(4-chloro-2,6-diethylphenyl)-5-methoxy-2,6-dimethyl-3-pyridinecarboxamide,
N-(4-bromo-2,6-diethylphenyl)-4-chloro-5-methoxy-2,6-dimethyl-3-pyridinecarboxamide,
4-chloro-N-(2,6-diethyl-4-methylphenyl)-5-methoxy-2,6-dimethyl-3-pyridinecarboxamide,
4-chloro-N-(2,6-diethyl-4-methoxyphenyl)-5-methoxy-2,6-dimethyl-3-pyridinecarboxamide,
4-chloro-N-(2,6-diethyl-4-iodophenyl)-5-methoxy-2,6-dimethyl-3-pyridinecarboxamide,
4-chloro-N-(2,6-diethyl-4-fluorophenyl)-5-methoxy-2,6-dimethyl-3-pyridinecarboxamide,
N-(3-bromo-4-methyl-2,6-diethylphenyl)-4-chloro-5-methoxy-2,6-dimethyl-3-pyridinecarboxamide,
4-chloro-5-ethoxy-N-(2,6-diethylphenyl)-2,6-dimethyl-3-pyridinecarboxamide,
4-chloro-N-(4-chloro-2,6-diethylphenyl)-5-ethoxy-2,6-dimethyl-3-pyridinecarboxamide,
4-chloro-5-ethoxy-N-(2,6-diethyl-4-iodophenyl)-2,6-dimethyl-3-pyridinecarboxamide,
4-chloro-5-ethoxy-N-(2,6-diethyl-4-methylphenyl)-2,6-dimethyl-3-pyridinecarboxamide,
4-chloro-5-ethoxy-N-(2,6-diethyl-4-methoxyphenyl)-2,6-dimethyl-3-pyridinecarboxamide,
4-chloro-5-ethoxy-N-(2,6-diethyl-4-fluorophenyl)-2,6-dimethyl-3-pyridinecarboxamide,
5-allyl-4-chloro-N-(2,6-diethylphenyl-4-fluorophenyl)-2,6-dimethyl-3-pyridinecarboxamide,
5-allyl-4-bromo-N-(2,6-diethylphenyl)-2,6-dimethyl-3-pyridinecarboxamide,
5-allyl-4-bromo-N-(4-bromo-2,6-diethylphenyl)-2,6-dimethyl-3-pyridinecarboxamide,
5-allyl-4-bromo-N-(4-chloro-2,6-diethylphenyl)-2,6-dimethyl-3-pyridinecarboxamide,
5-allyl-4-bromo-N-(2,6-diethyl-4-methylphenyl)-2,6-dimethyl-3-pyridinecarboxamide,
5-allyl-4-bromo-N-(2,6-diethyl-4-methoxyphenyl)-2,6-dimethyl-3-pyridinecarboxamide, 5-allyl-4-bromo-N-(2,6-diethyl-4-fluorophenyl)-2,6-dimethyl-3-pyridinecarboxamide,
4-bromo-N-(2,6-diethylphenyl)-2,6-dimethyl-5-(2-propynyl)-3-pyridinecarboxamide,
4-bromo-N-(2,6-diethyl-4-fluorophenyl)-2,6-dimethyl-5-(2-propynyl)-3-pyridinecarboxamide,
4-bromo-5-ethoxy-N-(2,6-diethylphenyl)-2,6-dimethyl-3-pyridinecarboxamide,
4-bromo-5-(2-butenyl)-N-(2,6-diethylphenyl)-2,6-dimethyl-3-pyridinecarboxamide,
4-bromo-N-(2,6-diethyl-4-fluorophenyl)-2,6-dimethyl-5-methoxy-3-pyridinecarboxamide,
4-bromo-5-(2-butenyl)-N-(2,6-diethyl-4-fluorophenyl)-2,6-dimethyl-3-pyridinecarboxamide,
5-allyl-4-bromo-N-(3-bromo-2,6-diethyl-4-methylphenyl)-2,6-dimethyl-3-pyridinecarboxamide,
5-allyl-N-(2,6-diethylphenyl)-4-fluoro-2,6-dimethyl-3-pyridinecarboxamide,
5-allyl-N-(2,6-diethyl-4-fluorophenyl)-4-fluoro-2,6-dimethyl-3-pyridinecarboxamide,
N-(2,6-diethylphenyl)-4-fluoro-2,6-dimethyl-5-(2-propynyl)-3-pyridinecarboxamide,
N-(2,6-diethyl-4-fluorophenyl)-4-fluoro-2,6-dimethyl-(2-propynyl)-3-pyridinecarboxamide,
N-(2,6-diethylphenyl)-4-fluoro-5-methoxy-2,6-dimethyl-3-pyridinecarboxamide,
5-ethoxy-N-(2,6-diethylphenyl)-4-fluoro-2,6-dimethyl-3-pyridinecarboxamide,
5-ethoxy-N-(2,6-diethyl-4-fluorophenyl)-4-fluoro-2,6-dimethyl-3-pyridinecarboxamide,
5-allyl-N-(4-chloro-2,6-diethylphenyl)-4-fluoro-2,6-dimethyl-3-pyridinecarboxamide,
5-allyl-N-(4-bromo-2,6-diethylphenyl)-4-fluoro-2,6-dimethyl-3-pyridinecarboxamide,
5-allyl-N-(2,6-diethyl-4-methoxyphenyl)-4-fluoro-2,6-dimethyl-3-pyridinecarboxamide,
5-allyl-N-(2,6-diethyl-4-methylphenyl)-4-fluoro-2,6-dimethyl-3-pyridinecarboxamide,
5-(2-butenyl)-N-(2,6-diethylphenyl)-4-fluoro-2,6-dimethyl-3-pyridinecarboxamide,
5-allyl-N-(2,6-diethylphenyl)-4-iodo-2,6-dimethyl-3-pyridinecarboxamide,
5-allyl-N-(2,6-diethyl-4-fluorophenyl)-4-iodo-2,6-dimethyl-3-pyridinecarboxamide,
N-(2,6-diethylphenyl)-4-iodo-2,6-dimethyl-5-(2-propynyl)-3-pyridinecarboxamide,
N-(2,6-diethyl-4-fluorophenyl)-4-iodo-2,6-dimethyl-5-(2-propynyl)-3-pyridinecarboxamide,
5-ethoxy-N-(2,6-diethyl-4-fluorophenyl)-4-iodo-2,6-dimethyl-3-pyridinecarboxamide,
N-(2,6-diethylphenyl)-4-iodo-5-methoxy-2,6-dimethyl-3-pyridinecarboxamide,
5-(2-butenyl)-N-(2,6-diethylphenyl)-4-iodo-2,6-dimethyl-3-pyridinecarboxamide,
5-allyl-4-chloro-N-(2,3-dimethylphenyl)-2,6-dimethyl-3-pyridinecarboxamide,
5-allyl-4-chloro-N-(2,4-dimethylphenyl)-2,6-dimethyl-3-pyridinecarboxamide,
5-allyl-4-chloro-N-(2-chlorophenyl)-2,6-dimethyl-3pyridinecarboxamide,
5-allyl-N-(2,3-dimethylphenyl)-4-fluoro-2,6-dimethyl-3-pyridinecarboxamide,
5-allyl-N-(2-chlorophenyl)-4-fluoro-2,6-dimethyl-3-pyridinecarboxamide,
5-(2-butenyl)-N-(2-chloropheryl)-4-fluoro-2,6-dimethyl-3-pyridinecarboxamide,
5-allyl-N-(3-chloro-2-methylphenyl)-4-fluoro-2,6-dimethyl-3-pyridinecarboxamide,
5-allyl-4-chloro-N-(3-chloro-2-methylphenyl)-2,6-dimethyl-3-pyridinecarboxamide,
4-chloro-N-(2,6-diethylphenyl)-5-(2,2,2-trifluoroethyl)-2,6-dimethyl-3-pyridinecarboxamide,
4-chloro-N-(2,6-diethyl-4-methylphenyl)-5-(2,2,2-trifluoroethyl)-2,6-dimethyl-3-pyridinecarboxamide,
4-chloro-N-(2,6-diethyl-4-methylphenyl)-5-(2,2,2-trifluoroethyl)-2,6-dimethyl-3-pyridinecarboxamide,
4-chloro-N-(4-chloro-2,6-diethylphenyl)-5-(2,2,2-trifluoroethyl)-2,6-dimethyl-3-pyridinecarboxamide,
N-(4-bromo-2,6-diethylphenyl)-4-chloro-5-(2,2,2-trifluoroethyl)-2,6-dimethyl-3-pyridinecarboxamide,
4-chloro-N-(2,6-diethyl-4-iodophenyl)-5-(2,2,2-trifluoroethyl)-2,6-dimethyl-3-pyridinecarboxamide,
N-(3-bromo-4-methyl-2,6-diethylphenyl)-4-chloro-5-(2,2,2-trifluoroethyl)-2,6-dimethyl-3-pyridinecarboxamide,
4-chloro-N-(2,6-diethylphenyl)-5-trifluoromethyl-2,6-dimethyl-3-pyridinecarboxamide,
5-allyl-4-chloro-N-(2,6-diethylphenyl)-2,6-bis-(trifluoromethyl)-3-pyridinecarboxamide,
5-allyl-4-chloro-N-(2,6-diethylphenyl)-6-trifluoromethyl-2-methyl-3-pyridinecarboxamide,
5-allyl-4-chloro-N-(2,6-diethylphenyl)-2-trifluoromethyl-6-methyl-3-pyridinecarboxamide,
5-allyl-4-chloro-N-(2-ethyl-6-methoxyphenyl)-2,6-dimethyl-3-pyridinecarboxamide,
5-allyl-4-chloro-N-(2,6-dimethoxyphenyl)-2,6-dimethyl-3-pyridinecarboxamide,
N-(4-bromo-2,6-diethylphenyl)-4-chloro-2,6-diethyl-5-(2-propynyl)-3-pyridinecarboxamide 1-oxide,
5-allyl-4-chloro-N-(2,6-diethyl-4-methoxyphenyl)-2,6-dimethyl-3-pyridinecarboxamide 1-oxide,
4-chloro-N-(2,6-diethyl-4-methoxyphenyl)-2,6-dimethyl-5-(2-propynyl)-3-pyridinecarboxamide 1-oxide,
4-chloro-N-(2,6-diethyl-4-methylphenyl)-2,6-dimethyl-5-(2-propynyl)-3-pyridinecarboxamide 1-oxide,
4-chloro-N-(2,6-diethyl-4-iodophenyl)-2,6-dimethyl-5-(2-propynyl)-3-pyridinecarboxamide 1-oxide,
4-chloro-N-(2,6-diethyl-4-fluorophenyl)-2,6-dimethyl-5-(2-propynyl)-3-pyridinecarboxamide 1-oxide,
4-chloro-N-(3-bromo-4-methyl-2,6-diethylphenyl)-2,6-dimethyl-5-(2-propynyl)-3-pyridinecarboxamide 1-oxide,
5-allyl-N-(3-bromo-4-methyl-2,6-diethylphenyl)-4-chloro-2,6-dimethyl-3-pyridinecarboxamide 1-oxide,
5-(2-butenyl)-4-chloro-N-(2,6-diethylphenyl)-2,6-dimethyl-3-pyridinecarboxamide 1-oxide,
5-(2-butenyl)-4-chloro-N-(4-chloro-2,6-diethylphenyl)-2,6-dimethyl-3-pyridinecarboxamide 1-oxide,
5-(2-butenyl)-N-(4-bromo-2,6-diethylphenyl)-4-chloro-2,6-dimethyl-3-pyridinecarboxamide 1-oxide,
5-(2-butenyl)-4-chloro-N-(2,6-diethyl-4-methylphenyl)-2,6-dimethyl-3-pyridinecarboxamide 1-oxide,
5-(2-butenyl)-4-chloro-N-(2,6-diethyl-4-methoxyphenyl)-2,6-dimethyl-3-pyridinecarboxamide 1-oxide,
5-(2-butenyl)-4-chloro-N-(2,6-diethyl-4-fluorophenyl)-2,6-dimethyl-3-pyridinecarboxamide 1-oxide,
N-(3-bromo-2,6-diethyl-4-methylphenyl)-5-(2-butenyl)-4-chloro-2,6-dimethyl-3-pyridinecarboxamide 1-oxide,
5-(2-butenyl)-4-chloro-N-(2,6-diethyl-4-iodophenyl)-2,6-dimethyl-3-pyridinecarboxamide 1-oxide,
4-chloro-N-(2,6-diethylphenyl)-5-methoxy-2,6-dimethyl-3-pyridinecarboxamie 1-oxide,
4-chloro-N-(4-chloro-2,6-diethylphenyl)-5-methoxy-2,6-dimethyl-3-pyridinecarboxamide 1-oxide, N-(4-bromo-2,6-diethylphenyl)-4-chloro-5-methoxy-2,6-dimethyl-3-pyridinecarboxamide 1-oxide,
4-chloro-N-(2,6-diethyl-4-methylphenyl)-5-methoxy-2,6-dimethyl-3-pyridinecarboxamide 1-oxide,
4-chloro-N-(2,6-diethyl-4-methoxyphenyl)-5-methoxy-2,6-dimethyl-3-pyridinecarboxamide 1-oxide,
4-chloro-N-(2,6-diethyl-4-iodophenyl)-5-methoxy-2,6-dimethyl-3-pyridinecarboxamide 1-oxide,
4-chloro-N-(2,6-diethyl-4-fluorophenyl)-5-methoxy-2,6-dimethyl-3-pyridinecarboxamide 1-oxide,
N-(3-bromo-4-methyl-2,6-diethylphenyl)-4-chloro-5-methoxy-2,6-dimethyl-3-pyridinecarboxamide 1-oxide,
4-chloro-5-ethoxy-N-(2,6-diethylphenyl)-2,6-dimethyl-3-pyridinecarboxamide 1-oxide,
4-chloro-N-(4-chloro-2,6-diethylphenyl)-5-ethoxy-2,6-dimethyl-3-pyridinecarboxamide 1-oxide,
4-chloro-5-ethoxy-N-(2,6-diethyl-4-iodophenyl)-2,6-dimethyl-3-pyridinecarboxamide 1-oxide,
4-chloro-5-ethoxy-N-(2,6-diethyl-4-methyphenyl)-2,6-dimethyl-3-pyridinecarboxamide 1-oxide,
4-chloro-5-ethoxy-N-(2,6-diethyl-4-methoxyphenyl)-2,6-dimethyl-3-pyridinecarboxamide 1-oxide,
4-chloro-5-ethoxy-N-(2,6-diethyl-4-fluorophenyl)-2,6-dimethyl-3-pyridinecarboxamide 1-oxide,
5-allyl-4-bromo-N-(2,6-diethylphenyl)-2,6-dimethyl-3-pyridinecarboxamide 1-oxide,
5-allyl-4-bromo-N-(4-bromo-2,6-diethylphenyl)-2,6-dimethyl-3-pyridinecarboxamide 1-oxide,
5-allyl-4-bromo-N-(4-chloro-2,6-diethylphenyl)-2,6-dimethyl-3-pyridinecarboxamie 1-oxide,
5-allyl-4-bromo-N-(2,6-diethyl-4-methylphenyl)-2,6-dimethyl-3-pyridinecarboxamide 1-oxide,
5-allyl-4-bromo-N-(2,6-diethyl-4-methoxyphenyl)-2,6-dimethyl-3-pyridinecarboxamide 1-oxide,
5-allyl-4-bromo-N-(2,6-diethyl-4-fluorophenyl)-2,6-dimethyl-3-pyridinecarboxamide 1-oxide,
4-bromo-N-(2,6-diethylphenyl)-2,6-dimethyl-5-(2-propynyl)-3-pyridinecarboxamide 1-oxide,
4-bromo-N-(2,6-diethyl-4-fluorophenyl)-2,6-dimethyl-5-(2-propynyl)-3-pyridinecarboxamide 1-oxide,
4-bromo-5-ethoxy-N-(2,6-diethylphenyl)-2,6-dimethyl-3-pyridinecarboxamide 1-oxide,
4-bromo-5-(2-butenyl)-N-(2,6-diethylphenyl)-2,6-dimethyl-3-pyridinecarboxamide 1-oxide,
4-bromo-N-(2,6-diethyl-4-fluorophenyl)-2,6-dimethyl-5-methoxy-3-pyridinecarboxamide 1-oxide,
4-bromo-5-(2-butenyl)-N-(2,6-diethyl-4-fluorophenyl)-2,6-dimethyl-3-pyridinecarboxamide 1-oxide,
5-allyl-4-bromo-N-(3-bromo-2,6-diethyl-4-methylphenyl)-2,6-dimethyl-3-pyridinecarboxamide 1-oxide,
5-allyl-N-(2,6-diethylphenyl -4-fluoro-2,6-dimethyl-3-pyridinecarboxamide 1-oxide,
5-allyl-N-(2,6-diethyl-4-fluorophenyl)-4-fluoro-2,6-dimethyl-3-pyridinecarboxamide 1-oxide,
N-(2,6-diethylphenyl)-4-fluoro-2,6-dimethyl-5-(2-propynyl)-3-pyridinecarboxamide 1-oxide,
N-(2,6-diethyl-4-fluorophenyl)-4-fluoro-2,6-dimethyl-5-(2-propynyl)-3-pyridinecarboxamide 1-oxide,
N-(2,6-diethylphenyl)-4-fluoro-5-methoxy-2,6-dimethyl-3-pyridinecarboxamide 1-oxide,
5-ethoxy-N-(2,6-diethylphenyl)-4-fluoro-2,6-dimethyl-3-pyridinecarboxamide 1-oxide,
5-ethoxy-N-(2,6-diethyl-4-fluorophenyl)-4-fluoro-2,6-dimethyl-3-pyridinecarboxamide 1-oxide,
5-allyl-N-(4-chloro-2,6-diethylphenyl)-4-fluoro-2,6-dimethyl-3-pyridinecarboxamide 1-oxide,
5-allyl-N-(4-bromo-2,6-diethylphenyl)-4-fluoro-2,6-dimethyl-3-pyridinecarboxamide 1-oxide,
5-allyl-N-(2,6-diethyl-4-methoxyphenyl)-4-fluoro-2,6-dimethyl-3-pyridinecarboxamide 1-oxide,
5-allyl-N-(2,6-diethyl-4-methylphenyl)-4-fluoro-2,6-dimethyl-3-pyridinecarboxamide 1-oxide,
5-(2-butenyl)-N-(2,6-diethylphenyl)-4-fluoro-2,6-dimethyl-3-pyridinecarboxamide 1-oxide,
5-allyl-N-(2,6-diethylphenyl)-4-iodo-2,6-dimethyl-3-pyridinecarboxamide 1-oxide,
5-allyl-N-(2,6-diethyl-4-fluorophenyl)-4-iodo-2,6-dimethyl-3-pyridinecarboxamide 1-oxide,
N-(2,6-diethylphenyl)-4-iodo-2,6-dimethyl-5-(2-propynyl)-3-pyridinecarboxamide 1-oxide,
N-(2,6-diethyl-4-fluorophenyl)-4-iodo-2,6-dimethyl-5-(2-propynyl)-3-pyridinecarboxamide 1-oxide,
5-ethoxy-N-(2,6-diethylphenyl)-4-iodo-2,6-dimethyl-3-pyridinecarboxamide 1-oxide,
N-(2,6-diethylphenyl)-4-iodo-5-methoxy-2,6-dimethyl-3-pyridinecarboxamide 1-oxide,
5-(2-butenyl)-N-(2,6-diethylphenyl)-4-iodo-2,6-dimethyl-3-pyridinecarboxamide 1-oxide,
5-allyl-4-chloro-N-(2,3-dimethylphenyl)-2,6-dimethyl-3-pyridinecarboxamide 1-oxide,
5-allyl-4-chloro-N-(2,4-dimethylphenyl)-2,6-dimethyl-3-pyridinecarboxamide 1-oxide,
5-allyl-4-chloro-N-(2-chlorophenyl)-2,6-dimethyl-3-pyridinecarboxamide 1-oxide,
5-allyl-N-(2,3-dimethylphenyl)-4-fluoro-2,6-dimethyl-3-pyridinecarboxamide 1-oxide,
5-allyl-N-(2-chlorophenyl)-4-fluoro-2,6-dimethyl-3-pyridinecarboxamide 1-oxide,
5-(2-butenyl)-N-(2-chlorophenyl)-4-fluoro-2,6-dimethyl-3-pyridinecarboxamide 1-oxide,
5-allyl-N-(3-chloro-2-methylphenyl)-4-fluoro-2,6-dimethyl-3-pyridinecarboxamide 1-oxide,
5-allyl-4-chloro-N-(3-chloro-2-methylphenyl)-2,6-dimethyl-3-pyridinecarboxamide 1-oxide,
4-chloro-N-(2,6-diethylphenyl)-5-(2,2,2-trifluoroethyl)-2,6-dimethyl-3-pyridinecarboxamide 1-oxide,
4-chloro-N-(1-oxide
4chloro-N-(2,6-diethyl-4-methylphenyl)-5-(2,2,2-trifluoroethyl)-2,6-dimethyl-3-pyridinecarboxamide 1-oxide,
4-chloro-N-(2,6-diethyl-4-methoxyphenyl)-5-(2,2,2-trifluoroethyl)-2,6-dimethyl-3-pyridinecarboxamide 1-oxide,
4-chloro-N-(4-chloro-2,6-diethylphenyl)-5-(2,2,2-trifluoroethyl)-2,6-dimethyl-3-pyridinecarboxamide 1-oxide,
N-(4-bromo-2,6-diethylphenyl)-4-chloro-5-(2,2,2-trifluoroethyl-2,6-dimethyl-3-pyridinecarboxamide 1-oxide,
4-chloro-N-(2,6-diethyl-4-iodophenyl)-5-(2,2,2-trifluoroethyl)-2,6-dimethyl-3-pyridinecarboxamide 1-oxide,
N-(3-bromo-4-methyl-2,6-diethylphenyl)-4-chloro-5-(2,2,2-trifluoroethyl)-2,6-dimethyl-3-pyridinecarboxamide 1-oxide,
4-chloro-N-(2,6-diethylphenyl)-5-trifluoromethyl-2,6-dimethyl-3-pyridinecarboxamide 1-oxide,
5-allyl-4-chloro-N-(2,6-diethylphenyl)-2,6-bis-(trifluoromethyl)-3-pyridinecarboxamide 1-oxide,
5-allyl-4-chloro-N-(2,6-diethylphenyl)-6-trifluoromethyl-2-methyl-3-pyridinecarboxamide 1-oxide,
5-allyl-4-chloro-N-(2,6-diethylphenyl)-2-trifluoromethyl-6-methyl-3-pyridinecarboxamide 1-oxide, 5-allyl-4-chloro-N-(2-ethyl-6-methoxyphenyl)-2,6-dimethyl-3-pyridinecarboxamide 1-oxide, 5-allyl-4-chloro-N-(2,6-dimethoxyphenyl)-2,6-dimethyl-3-pyridinecarboxamide 1-oxide, 5-allyl-4-chloro-2-cyclopropyl-N-(2,6-diethylphenyl)-6-methyl-3-pyridinecarboxamide, 2-allyl-4-chloro-N-(2,6-diethylphenyl)-5,6-dimethyl-3-pyridinecarboxamide, 4-chloro-5-(3-chloropropyl)-N-(2,6-diethylphenyl)-2,6-dimethyl-3-pyridinecarboxamide, 5-allyl-4-chloro-2,6-dimethyl-N-(2,6-dimethylphenyl)-3-pyridinecarboxamide, 5-allyl-4-chloro-N-(2-ethyl-6-methylphenyl)-2,6-dimethyl-3-pyridinecarboxamide, 5-allyl-N-(3-bromo-2,6-diethylphenyl)-4-chloro-2,6-dimethyl-3-pyridinecarboxamide, 4-chloro-2,6-dimethyl-N-phenyl-5-phenylmethyl-3-pyridinecarboxamide, 4-chloro-N-(2,6-diethylphenyl)-5,6-dimethyl-2-(2-pyridyl)-3-pyridinecarboxamide, 4-chloro-N-(2,6-diethylphenyl)-2,5-dimethyl-6-(2-pyridyl)-3-pyridinecarboxamide, 4-chloro-N-(2,6-diethylphenyl)-2-(2-furyl)-5,6-dimethyl3-pyridinecarboxamide, and 4-chloro-N-(2,6-diethylphenyl)-6-(2-furyl)-2,5-dimethyl3-pyridinecarboxamide.

This invention is illustrated further by examples hereinafter.

Physico-chemical data on Compounds obtained by Examples are shown in Tables 1 and 2.

Growth-regulating activities on plants of the compounds of the invention are shown in Table 3.

Furthermore, the evaluation method growth regulating activity is as follows;

A carrier was prepared by mixing 50 parts (by weight) of talc, 25 parts of bentonite, 2 parts of Solpole-9047 (Toho Chemical Co., Ltd, Japan) and 3 parts of Solpole-5039 (Toho Chemical Co., Ltd, Japan). 50 parts of a test compound and 200 parts of the carrier were mixed to obtain a 20% wettable powder, followed by dispersing the powder in distilled water to make a dispersion of the defined concentrations.

Seeds of *Oryza sativa* L., *Echinochloa crus-galli* L., and *Raphanus sativus* L. were germinated in a laboratory dish, to which the dispersion was added. After breeding for 7 days in a thermostatic box kept at 25° C. under illumination of fluorescent tubes, the growth of plant was observed.

In the column of "Evaluation" of Table 3, the designation 1 denotes no influence, 2 denotes 25% growth inhibition, 3 denotes 50% growth inhibition, 4 denotes 75% growth inhibition and 5 denotes 100% growth inhibition.

EXAMPLE 1

5-Allyl-4-chloro-N-(2,6-diethyl-4-methylphenyl)-2,6-dimethyl-3-pyridinecarboxamide (Method A)

A mixture of 0.85 g (2.41 m mol) of 5-allyl-N-(2,6-diethyl-4-methylphenyl)-1,4-dihydro-2,6-dimethyl-4-oxo-3-pyridinecarboxamide and 5 ml of phosphorus oxychloride was heated under reflux for an hour. An excess of phosphorus oxychloride was removed under vacuum, and the residue was dissolved in 100 ml of methylene chloride. Then the resulting solution was added into 150 ml of saturated sodium bicarbonate solution, followed by stirring for an hour at room temperature. The organic layer was washed with water, dried and concentrated by the conventional method. The resultant crystalline residue was recrystallized from ethyl acetate to give 0.84 g of the title compound, m.p. 192.5°–194° C.

EXAMPLES 2-55

Compounds were obtained by the method as described in the column "Method" of Table 1. Their physico-chemical data are shown in Tables 1 and 2, and their growth-regulating activities on plants are shown in Table 3.

TABLE 1

| Example No. | $R_1$ | $R_2$ | $R_3$ | $R_4$ | $R_5$ | $R_6$ | $R_7$ | $R_8$ | X | mp (°C.) | Method |
|---|---|---|---|---|---|---|---|---|---|---|---|
| 1 | $CH_3$ | $C_2H_5$ | H | $CH_3$ | H | $C_2H_5$ | $CH_2=CH-CH_2-$ | $CH_3$ | Cl | 192.5–194 | A |
| 2 | " | " | " | H | " | " | " | " | " | 200–204.5 | " |
| 3 | " | " | " | Cl | " | " | " | " | " | 145.5–148 | " |
| 4 | " | " | " | Br | " | " | " | " | " | 201–203 | " |
| 5 | " | " | " | H | " | " | $HC\equiv C-CH_2-$ | " | " | 242–244 | " |
| 6* | " | " | " | Cl | " | " | $CH_2=CH-CH_2-$ | " | " | 187.5–188.5 | C |
| 7 | " | " | " | I | " | " | " | " | " | 222–224 | A |
| 8 | " | " | " | Br | " | " | $n\text{-}C_4H_9$ | " | Cl | 228.5–229 | A |
| 9 | " | H | " | H | " | H | H | " | " | 157–158 | " |
| 10 | " | $CH_3$ | $CH_3$ | " | " | " | $C_2H_5$ | " | " | 193–197 | " |
| 11 | " | $C_2H_5$ | H | " | " | $C_2H_5$ | H | " | " | 210.5–215 | " |
| 12 | " | " | " | " | " | " | $CH_3$ | " | " | 222–229.5 | " |
| 13 | " | " | " | " | " | " | $C_2H_5$ | " | " | 232–232.5 | " |
| 14 | " | " | " | " | " | " | $n\text{-}C_3H_7$ | " | " | | " |
| 15 | " | " | " | " | " | " | $iso\text{-}C_4H_9$ | " | " | 162–164.5 | " |
| 16 | " | " | " | " | " | " | $iso\text{-}C_5H_{11}$ | " | " | 196.5–198 | " |
| 17 | " | " | " | " | " | " | Br | " | " | | " |
| 18 | " | " | " | " | " | " | Ph | " | " | 210–211 | " |
| 19 | " | " | " | " | " | " | $CH_2Ph$ | " | " | 213.5–215.5 | " |
| 20 | $C_2H_5$ | " | " | " | " | " | $CH_3$ | " | " | | " |
| 21 | $n\text{-}C_3H_7$ | " | " | " | " | " | H | " | " | | " |
| 22 | " | " | " | " | " | " | $CH_3$ | " | " | | " |
| 23 | $n\text{-}C_4H_9$ | " | " | " | " | " | H | " | " | | " |
| 24 | " | " | " | " | " | " | Br | " | " | | " |
| 25 | $CH_3$ | " | " | " | " | " | $CH_3$ | $C_2H_5$ | " | 244–246 | " |

TABLE 1-continued

| Example No. | R₁ | R₂ | R₃ | R₄ | R₅ | R₆ | R₇ | R₈ | X | mp (°C.) | Method |
|---|---|---|---|---|---|---|---|---|---|---|---|
| 26 | (2-Br, 4-CH₃-phenyl) | H | " | " | " | H | H | CH₃ | " | 191–192 | " |
| 27 | CH₃ | C₂H₅ | " | " | " | C₂H₅ | —(CH₂)₄— | | " | 214–216 | " |
| 28 | " | " | " | Br | " | " | CH₃ | CH₃ | " | 277.5–279 | " |
| 29 | " | " | " | " | " | " | C₂H₅ | " | " | 244.5–246 | " |
| 30 | " | " | " | " | " | " | C₃H₇ | " | " | 206.5–209 | " |
| 31 | " | " | " | H | " | " | C₄H₉ | " | " | | " |
| 32 | " | " | " | Br | " | " | iso-C₄H₉ | " | " | | " |
| 33 | " | " | " | " | " | " | iso-C₅H₁₁ | " | " | 201–201.5 | " |
| 34 | n-C₃H₇ | " | " | " | " | " | CH₃ | " | " | | " |
| 35 | n-C₄H₉ | " | " | " | " | " | C₂H₅ | " | " | | " |
| 36 | Ph | " | " | H | " | " | H | " | Br | | " |
| 37* | C₂H₅ | " | " | " | " | " | CH₃ | " | Cl | 232.5–233.5 | C |
| 38 | " | " | " | " | " | " | n-C₃H₇ | " | " | | A |
| 39 | " | " | " | " | " | " | C₂H₅ | " | " | | " |
| 40 | CH₃ | " | " | " | " | " | —(CH₂)₃— | | " | 233–234.5 | " |
| 41 | " | " | Br | CH₃ | " | " | CH₂=CH—CH₂— | CH₃ | " | 204.5–205.5 | A |
| 42 | " | " | H | Cl | " | " | n-C₃H₇ | " | " | 198–200 | " |
| 43 | " | " | " | OCH₃ | " | " | CH₂=CH—CH₂— | " | " | | " |
| 44 | " | " | " | H | " | " | H | CF₃ | " | 246–247 | " |
| 45 | " | " | " | F | " | " | CH₂=CH—CH₂— | CH₃ | " | | " |
| 46 | " | " | " | " | " | " | iso-C₄H₉ | " | " | 172.5–174 | " |
| 47** | " | " | " | H | " | " | CH₂=CH—CH₂— | " | " | 200.5–201 | " |
| 48 | " | " | " | " | " | " | CH₂=CHCH₂CH₂— | " | " | 181–185 | " |
| 49 | " | " | " | " | " | " | CH₃CH=CHCH₂— | " | " | 198–201 | " |
| 50 | " | " | " | " | " | " | CH₂=C(CH₃)CH₂— | " | " | | " |
| 51 | " | " | " | " | " | " | (CH₃)₂C=CHCH₂— | " | " | 166f–173.5 | " |
| 52 | —CH₂OCH₃ | " | " | " | " | " | CH₃ | " | " | 203.5–208.5 | " |
| 53 | CF₃ | " | " | " | " | " | n-C₃H₇ | " | " | | " |
| 54* | CH₃ | " | " | " | " | " | CH≡CCH₂— | " | " | 245.5–247 | C |
| 55* | " | " | " | " | " | " | CH₂=CHCH₂— | " | " | | " | note
*1-oxide
**hydrochloride salt

TABLE 2

| Example No. | IR ν-value (cm⁻¹) | Method | NMR Chemical shift δ value | Solvent |
|---|---|---|---|---|
| 1 | 1643, 1650 | KBr | 1.22(t, 6H), 2.33(s, 3H), 2.55(s, 3H), 2.63(s, 3H), 2.70(q, 4H), 3.53(d, 2H), 4.73–5.20(m, 2H), 5.50–6.17(m, 1H), 6.93(s, 2H), 7.10(br, 1H) | CDCl₃ |
| 2 | 1655 | " | 1.22(t, 6H), 2.55(s, 3H), 2.63(s, 3H), 2.76(q, 4H), 3.55(d, 2H), 4.76–5.23 (m, 2H), 5.50–6.23(m, 1H), 7.14 (s, 3H), 7.22(br, 1H) | " |
| 3 | 1638 | " | 1.10(t, 6H), 2.50(s, 6H), 2.57(q, 4H), 3.43(d, 2H), 4.68–5.17(m, 2H), 5.40–6.10(m, 1H), 6.97(s, 2H), 7.85(br, 1H) | " |
| 4 | 1647, 1653 | " | 1.18(t, 6H), 2.54(s, 3H), 2.58(s, 3H), 2.70(q, 4H), 3.52(d, 2H), 4.73–5.29 (d, 2H), 5.47–6.20(m, 1H), 7.26 (br, 4H) | " |
| 5 | 1650 | " | 1.22(t, 6H), 2.28(t, 1H), 2.67(s, 6H), 2.76(q, 4H), 3.70(q, 2H), 7.10(s, 3H), 9.68(br, 1H) | CDCl₃ -DMSO-d₆ |
| 6 | 1657, 1683 | " | 1.29(t, 6H), 2.41(s, 3H), 2.53(s, 3H), 2.76(q, 4H), 3.49(d, 2H), 4.73–5.30 (m, 2H), 5.37–6.20(m, 1H), 7.10 (s, 2H), 9.26(br, 1H) | CDCl₃ |
| 7 | 1650 | " | 1.17(t, 6H), 2.52(s, 3H), 2.57(s, 3H), 2.65(q, 4H), 2.50(d, 2H), 4.65–5.25 (m, 2H), 5.30–6.20(m, 1H), 7.10 (br, 1H), 7.39(s, 2H) | " |
| 8 | 1647 | " | 0.70–1.75(m, 4H), 1.08(t, 3H), 1.20 (t, 6H), 2.56(s, 3H), 2.60(s, 3H), 2.40–3.00(m, 6H), 7.20(s, 2H), 9.43 (br, 1H) | " |
| 9 | 1653 | " | 2.50(s, 3H), 2.56(s, 3H), 7.00(s, 1H), 7.07–7.13(m, 5H), 7.87(br, 1H) | " |
| 10 | 1653 | " | 1.15(t, 3H), 2.20(s, 3H), 2.30(s, 3H), | " |

TABLE 2-continued

| Example No. | IR ν-value (cm⁻¹) | Method | NMR Chemical shift δ value | Solvent |
|---|---|---|---|---|
| | | | 2.57(s, 6H), 2.78(q, 2H), 7.00–7.67 (m, 4H) | |
| 11 | 1653 | " | 1.21(t, 6H), 2.50(s, 3H), 2.67(s, 3H), 2.73(q, 4H), 7.00–7.33(m, 5H) | " |
| 12 | 1650 | " | 1.00(t, 6H), 2.12(s, 3H), 2.32(s, 3H), 2.37(s, 3H), 2.47(q, 4H), 6.85–7.30 (m, 3H), 8.06(br, 1H) | " |
| 13 | 1650 | " | 1.16(t, 3H), 1.21(t, 6H), 2.60(s, 3H), 2.66(s, 3H), 2.80(q, 4H), 2.86(q, 2H), 7.13(br, 1H), 7.20(s, 3H) | " |
| 14 | 1655 | " | 0.80–1.90(m, 5H), 1.18(t, 6H), 2.40–2.95(m, 6H), 2.55(s, 3H), 2.57(s, 3H), 7.13(s, 3H), 7.30(br, 1H) | " |
| 15 | 1650, 1655 | " | 0.97(d, 6H), 1.21(t, 6H), 2.07(sep, 1H), 2.53–3.07(m, 6H), 2.56(s, 3H), 2.63(s, 3H), 7.00–7.40(m, 4H) | " |
| 16 | 1655 | " | 0.70–1.90(m, 3H), 0.97(d, 6H), 1.19 (t, 6H), 2.53(s, 3H), 2.57(s, 3H), 2.40–3.00(m, 6H), 7.13(m, 4H) | " |
| 17 | 1650 | " | 1.20(t, 6H), 2.62(s, 3H), 2.68(s, 3H), 2.73(q, 4H), 7.08(s, 3H), 9.53(br, 1H) | CDCl₃ -DMSO-d₆ |
| 18 | 1640 | " | 1.18(t, 6H), 2.28(s, 3H), 2.70(s, 3H), 2.75(q, 4H), 6.90–7.80(m, 9H) | CDCl₃ |
| 19 | 1682 | " | 1.20(t, 6H), 2.49(s, 3H), 2.63(s, 3H), 2.75(q, 4H), 4.19(s, 2H), 6.90–7.50 (m, 9H) | " |
| 20 | 1647 | " | 1.22(t, 6H), 1.30(t, 3H), 2.34(s, 3H), 2.56(s, 3H), 2.76(q, 4H), 2.90(q, 2H), 7.00(br, 1H), 7.16(s, 3H) | " |
| 21 | 1650 | " | 0.95(t, 3H), 1.19(t, 6H), 1.76(six, 2H), 2.49(s, 3H), 2.40–3.10(m, 6H), 7.00(s, 1H), 7.10(br, 1H), 7.16 (s, 3H) | " |
| 22 | 1643 | " | 0.92(t, 3H), 1.13(t, 6H), 1.73(six, 2H), 2.26(s, 3H), 2.47(s, 3H), 2.50–3.00(m, 6H), 7.00–7.17(m, 3H), 7.35 (br, 1H) | " |
| 23 | 1643 | " | 0.93(t, 3H), 0.70–2.00(m, 4H), 1.24 (t, 6H), 2.53(s, 3H), 2.79(q, 4H), 2.98(t, 2H), 7.00(br, 1H), 7.08 (s, 1H), 7.18(s, 3H) | " |
| 24 | 1655 | " | 0.70–2.10(m, 4H), 0.95(t, 3H), 1.25 (t, 6H), 2.72(s, 3H), 2.60–3.10 (m, 6H), 6.97(br, 1H), 7.13(s, 3H) | " |
| 25 | 1650 | " | 1.21(t, 6H), 1.24(t, 3H), 2.36(s, 3H), 2.63(s, 3H), 2.76(q, 4H), 2.84(q, 2H), 6.90–7.35(m, 4H) | " |
| 26 | 1673 | " | 2.50(s, 3H), 6.90–7.80(m, 10H), 8.27(br, 1H) | " |
| 27 | 1647 | " | 1.19(t, 6H), 1.60–2.10(m, 4H), 2.50–3.10(m, 8H), 2.68(s, 3H), 7.14(s, 3H), 7.77(br, 1H) | " |
| 28 | 1650 | " | 1.21(t, 6H), 2.34(s, 3H), 2.50(s, 3H), 2.60(s, 3H), 2.70(q, 4H), 7.18(s, 2H), 9.12(br, 1H) | " |
| 29 | 1652 | " | 1.11(t, 3H), 1.17(t, 6H), 2.55 (s, 6H), 2.45–3.03(m, 6H), 7.23(br, 3H) | " |
| 30 | 1640 | " | 0.80–1.80(m, 5H), 1.17(t, 6H), 2.40–3.00(m, 6H), 2.53(s, 3H), 2.59(s, 3H), 7.18(s, 2H), 8.92(br, 1H) | " |
| 31 | 1650 | " | 0.70–1.80(m, 7H), 1.19(t, 6H), 2.40–3.00(m, 6H), 2.57(s, 3H), 2.65(s, 3H), 7.13(s, 3H), 7.86(br, 1H) | " |
| 32 | 1650 | " | 0.95(d, 6H), 1.17(t, 6H), 1.60–3.00 (m, 7H), 2.60(s, 6H), 7.24(s, 2H), 8.07(br, 1H) | " |
| 33 | 1655 | " | 0.80–2.00(m, 5H), 0.98(d, 6H), 1.19 (t, 6H), 2.40–2.95(m, 6H), 2.53 (s, 3H), 2.56(s, 3H), 7.10(br, 1H) 7.22(s, 2H) | " |
| 34 | 1653 | " | 0.98(t, 3H), 1.20(t, 6H), 1.75(six, 2H), 2.30(s, 3H), 2.49(s, 3H), 2.50–2.93(m, 6H), 7.13(s, 2H), 9.13(br, 1H) | CDCl₃ -DMSO-d₆ |
| 35 | 1650 | " | 0.70–2.10(m, 10H), 1.20(t, 6H), 2.50–3.10(m, 8H), 2.56(s, 3H), 7.00(br, 1H), 7.27(s, 2H) | CDCl₃ |
| 36 | 1648 | " | 0.94(t, 6H), 2.15(q, 4H), 2.59(s, 3H), 6.75(br, 1H), 6.80–7.80(m, 8H) | " |

TABLE 2-continued

| Example No. | IR ν-value (cm⁻¹) | Method | NMR Chemical shift δ value | Solvent |
|---|---|---|---|---|
| 37 | 1653 | " | 1.20(t, 3H), 1.26(t, 6H), 2.32(s, 3H), 2.47(s, 3H), 2.82(q, 4H), 3.07(q, 2H), 7.13(s, 3H), 8.63(br, 1H) | " |
| 38 | 1652 | " | 0.70–2.00(m, 2H), 1.02(t, 3H), 1.17 (t, 6H), 1.26(t, 3H), 2.54(s, 3H), 2.20–3.10(m, 8H), 6.85–7.40(m, 4H) | " |
| 39 | 1643 | " | 1.09(t, 3H), 1.22(t, 6H), 1.30(t, 3H), 2.57(s, 3H), 2.30–3.20(m, 8H), 6.80–7.40(m, 4H) | " |
| 40 | 1650 | " | 1.14(t, 6H), 1.75–2.40(m, 2H), 2.40–3.25(m, 8H), 2.54(s, 3H), 6.85–7.35 (m, 3H), 7.47(br, 1H) | " |
| 41 | 1648 | " | 1.08(t, 3H), 1.13(t, 3H), 2.30–3.20 (m, 4H), 2.39(s, 3H), 2.50(s, 3H), 2.55(s, 3H), 3.47(d, 2H), 4.70–5.23 (m, 2H), 5.45–6.15(m, 1H), 6.97 (s, 1H), 7.42(br, 1H) | " |
| 42 | 1642 | " | 1.03(t, 3H), 1.20(t, 6H), 1.30–2.00 (m, 2H), 2.35–3.10(m, 2H), 2.54 (s, 3H), 2.57(s, 3H), 2.70(q, 4H), 6.85–7.30(m, 3H) | " |
| 43 | 1647 | " | 1.19(t, 6H), 2.52(s, 3H), 2.59(s, 3H), 2.68(q, 4H), 3.50(d, 2H), 3.77(s, 3H), 4.70–5.30(m, 2H), 5.40–6.20(m, 1H), 6.60(s, 2H), 7.12(br, 1H) | " |
| 44 | 1653 | " | 1.21(t, 6H), 2.74(q, 4H), 2.77(s, 3H), 6.85–7.30(m, 3H), 7.51(s, 1H), 9.23(br, 1H) | CDCl₃ -DMSO-d₆ |
| 45 | 1648 | " | 1.17(t, 6H), 2.52(s, 3H), 2.56(s, 3H), 2.68(q, 4H), 3.50(d, 2H), 4.70–5.20 (m, 2H), 5.50–6.20(m, 1H), 6.78 (d, 2H), 7.23(br, 1H) | CDCl₃ |
| 46 | 1640 | " | 0.97(d, 6H), 1.22(t, 6H), 1.50–2.50 (m, 1H), 2.55(s, 3H), 2.62(s, 3H), 2.40–3.00(m, 6H), 6.78(d, 2H), 6.93(br, 1H) | " |
| 47 | 1680, 1950, 2450 | " | 1.22(t, 6H), 2.75(q, 4H), 2.76(s, 3H), 2.97(s, 3H), 3.58(d, 2H), 4.75–5.30 (m, 2H), 5.40–6.10(m, 1H), 6.85–7.30 (m, 3H), 9.84(br, 1H) | " |
| 48 | 1650 | " | 1.21(t, 6H), 1.95–3.20(m, 4H), 2.57 (s, 3H), 2.63(s, 3H), 2.75(q, 4H), 4.70–5.30(m, 2H), 5.30–6.30(m, 1H), 6.90–7.50(m, 4H) | " |
| 49 | 1650 | " | 1.19(t, 6H), 1.50–1.90(m, 3H), 2.53 (s, 3H), 2.58(s, 3H), 2.73(q, 4H), 3.25–3.60(m, 2H), 5.20–5.60(m, 2H), 6.85–7.45(m, 4H) | " |
| 50 | 1640 | " | 1.17(t, 6H), 1.81(s, 3H), 2.47(s, 3H), 2.57(s, 3H), 2.73(q, 4H), 3.41(br, 2H), 4.28(br, 1H), 4.60–4.85(m, 1H), 6.85–7.40(m, 3H), 7.23(br, 1H) | " |
| 51 | 1653 | " | 1.20(t, 6H), 1.74(d, 6H), 2.52(s, 3H), 2.59(s, 3H), 2.72(q, 4H), 3.44(d, 2H), 4.50–5.20(m, 1H), 6.85–7.35(m, 4H) | " |
| 52 | 1650 | " | 1.23(t, 6H), 2.37(s, 3H), 2.58(s, 3H), 2.77(q, 4H), 3.41(s, 3H), 4.61(s, 2H), 6.90–7.35(m, 3H), 7.37(br, 1H) | " |
| 53 |  |  | 0.60–2.20(m, 5H), 1.18(t, 6H), 2.20–3.20(m, 6H), 2.63(s, 3H), 6.80–7.50 (m, 4H) | " |
| 54 |  |  | 1.21(t, 6H), 2.20–3.20(m, 5H), 2.58 (s, 3H), 2.62(s, 3H), 3.76(q, 2H), 6.90–7.25(m, 3H), 9.78(br, 1H) | CDCl₃ -DMSO-d₆ |
| 55 |  |  | 1.26(t, 6H), 2.40(s, 3H), 2.53(s, 3H), 2.78(q, 4H), 3.47(d, 2H), 4.65–5.30 (m, 2H), 5.30–6.10(m, 1H), 6.90–7.45 (m, 3H), 9.12(br, 1H) | CDCl₃ |

TABLE 3

| Example No. | Conc. (ppm) | Evaluation Plants | | |
|---|---|---|---|---|
| | | X | Y | Z |
| 1 | 20 | 5 | 5 | 5 |
| | 100 | 5 | 5 | 5 |
| 2 | 20 | 5 | 5 | 5 |
| | 100 | 5 | 5 | 5 |
| 3 | 20 | 5 | 5 | 5 |
| | 100 | 5 | 5 | 5 |

TABLE 3-continued

| Example No. | Conc. (ppm) | X | Y | Z |
|---|---|---|---|---|
| 4 | 20 | 5 | 5 | 5 |
|  | 100 | 5 | 5 | 5 |
| 5 | 20 | 5 | 5 | 5 |
|  | 100 | 5 | 5 | 5 |
| 6 | 20 | 5 | 5 | 5 |
|  | 100 | 5 | 5 | 5 |
| 7 | 20 | 5 | 5 | 5 |
|  | 100 | 5 | 5 | 5 |
| 8 | 20 | 5 | 5 | 5 |
|  | 100 | 5 | 5 | 5 |
| 9 | 20 | 5 | 5 | 5 |
|  | 100 | 5 | 5 | 5 |
| 10 | 20 | 5 | 5 | 5 |
|  | 100 | 5 | 5 | 5 |
| 11 | 20 | 5 | 5 | 5 |
|  | 100 | 5 | 5 | 5 |
| 12 | 20 | 5 | 5 | 5 |
|  | 100 | 5 | 5 | 5 |
| 13 | 20 | 5 | 5 | 5 |
|  | 100 | 5 | 5 | 5 |
| 14 | 20 | 5 | 5 | 5 |
|  | 100 | 5 | 5 | 5 |
| 15 | 20 | 5 | 5 | 5 |
|  | 100 | 5 | 5 | 5 |
| 16 | 20 | 4 | 5 | 5 |
|  | 100 | 5 | 5 | 5 |
| 17 | 20 | 3 | 4 | 4 |
|  | 100 | 4 | 5 | 5 |
| 19 | 20 | 1 | 1 | 2 |
|  | 100 | 2 | 2 | 3 |
| 20 | 20 | 5 | 5 | 5 |
|  | 100 | 5 | 5 | 5 |
| 21 | 20 | 5 | 5 | 5 |
|  | 100 | 5 | 5 | 5 |
| 22 | 20 | 5 | 5 | 5 |
|  | 100 | 5 | 5 | 5 |
| 23 | 20 | 5 | 5 | 5 |
|  | 100 | 5 | 5 | 5 |
| 24 | 20 | 3 | 5 | 1 |
|  | 100 | 4 | 5 | 2 |
| 25 | 20 | 4 | 5 | 4 |
|  | 100 | 5 | 5 | 5 |
| 26 | 20 | 1 | 4 | 1 |
|  | 100 | 1 | 4 | 1 |
| 27 | 20 | 4 | 5 | 5 |
|  | 100 | 5 | 5 | 5 |
| 28 | 20 | 4 | 5 | 5 |
|  | 100 | 5 | 5 | 5 |
| 29 | 20 | 5 | 5 | 5 |
|  | 100 | 5 | 5 | 5 |
| 30 | 20 | 4 | 5 | 4 |
|  | 100 | 5 | 5 | 5 |
| 31 | 20 | 4 | 5 | 5 |
|  | 100 | 5 | 5 | 5 |
| 34 | 20 | 4 | 4 | 3 |
|  | 100 | 5 | 5 | 4 |
| 35 | 20 | 2 | 5 | 1 |
|  | 100 | 3 | 5 | 2 |
| 36 | 20 | 5 | 5 | 4 |
|  | 100 | 5 | 5 | 5 |
| 37 | 20 | 5 | 5 | 5 |
|  | 100 | 5 | 5 | 5 |
| 38 | 20 | 5 | 5 | 5 |
|  | 100 | 5 | 5 | 5 |
| 39 | 20 | 5 | 5 | 5 |
|  | 100 | 5 | 5 | 5 |
| 40 | 20 | 5 | 5 | 5 |
|  | 100 | 5 | 5 | 5 |
| 41 | 20 | 5 | 5 | 4 |
|  | 100 | 5 | 5 | 5 |
| 42 | 20 | 5 | 5 | 5 |
|  | 100 | 5 | 5 | 5 |
| 43 | 20 | 5 | 5 | 5 |
|  | 100 | 5 | 5 | 5 |
| 45 | 20 | 5 | 5 | 5 |
|  | 100 | 5 | 5 | 5 |
| 46 | 20 | 5 | 5 | 5 |
|  | 100 | 5 | 5 | 5 |
| 47 | 20 | 5 | 5 | 5 |
|  | 100 | 5 | 5 | 5 |

X: *Oryza sativa* L.
Y: *Echinochloa crus-galli* L.
Z: *Raphanus sativus* L.

What we claim is:

1. A compound of the formula 1:

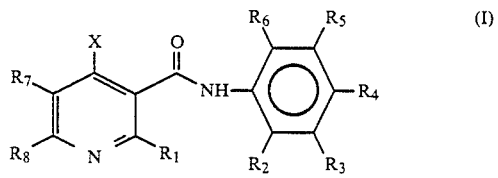

or 1-oxide or salt thereof, wherein $R_1$ is a $C_{1-11}$ alkyl group, a lower alkenyl group, a lower alkynyl group, a cycloalkyl group, a lower alkoxy-alkyl group, a lower alkylthioalkyl group, a phenyl group which can be unsubstituted or substituted by one or two groups selected from the group consisting of a halogen atom, a lower alkyl group and a lower alkoxy group, an aralkyl group whose nucleus can be unsubstituted or substituted by one or two groups selected from the group consisting of a halogen atom, a lower alkyl group and a lower alkoxy group, and a haloalkyl group; $R_2$, $R_3$, $R_4$, $R_5$ and $R_6$ are the same or different and are selected from the group consisting of a hydrogen atom, a halogen atom, a cyano group, a nitro group, an amine group, a lower alkyl group, a lower haloalkyl group, a hydroxy group, a lower alkoxy group, an aryloxy group, a carboxy group or a lower alkoxycarbonyl group; $R_7$ is a hydrogen atom, a halogen atom, a lower alkyl group, a phenyl group which can be unsubstituted or substituted by one or two groups selected from the group consisting of a halogen atom, a lower alkyl group and a lower alkoxy group, an aralkyl group whose nucleus can be unsubstituted or substituted by one or two groups selected from the group consisting of a halogen atom, a lower alkyl group and a lower alkoxy group, a lower alkenyl group, a lower alkynyl group, a lower alkoxy group or a haloalkyl group; $R_8$ is a $C_{1-11}$ alkyl group, a lower alkenyl group, a lower alkynyl group, a cycloalkyl group, a lower alkoxyalkyl group, a lower alkylthioalkyl group, a phenyl group which can be unsubstituted or substituted by one or two groups selected from the group consisting of a halogen atom, a lower alkyl group and a lower alkoxy group, an aralkyl group whose nucleus can be unsubstituted or substituted by one or two groups selected from the group consisting of a halogen atom, a lower alkyl group and a lower alkoxy group, a haloalkyl group; or $R_7$ and $R_8$ may be combined to form a group of $-(CH_2)_m-$ (wherein m is 3 or 4); and X is a halogen atom.

2. A compound of claim 1 wherein X is a chlorine atom.

3. A compound of claim 1 wherein X is a bromine atom.

4. A compound of claim 1 wherein

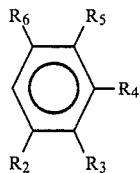

in the formula (I) is 2,6-diethylphenyl or 4-bromo-2,6-diethylphenyl.

5. A compound of claim 1 wherein

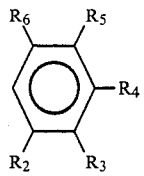

in the formula (I) is 4-chloro-2,6-diethylphenyl, 2,6-diethyl-4-methoxyphenyl or 2,6-diethyl-4-fluorophenyl.

6. A compound of claim 1 wherein $R_1$ and $R_8$ are methyl.

7. A compound of claim 1 wherein $R_7$ is ethyl, propyl, isobutyl, isopentyl, 2-butenyl, 3-butenyl, 2-methyl-2-propenyl, 3-methyl-2-butenyl, allyl or 2-propynyl.

8. A compound of claim 1 wherein X is a fluorine atom.

9. A compound of claim 1 wherein X is an iodine atom.

10. A compound of claim 1 which is:
4-chloro-5-ethyl-N-(2,6-diethylphenyl)-2,6-dimethyl-3-pyridinecarboxamide,
4-chloro-N-(2,6-diethylphenyl)-2,6-dimethyl-5-propyl-3-pyridinecarboxamide,
5-butyl-4-chloro-N-(2,6-diethylphenyl)-2,6-dimethyl-3-pyridinecarboxamide,
4-chloro-N-(2,6-diethylphenyl)-2,6-dimethyl-5-(2-methylpropyl)-3-pyridinecarboxamide,
4-chloro-N-(2,6-diethylphenyll)-2,6-dimethyl-5-(3-methylbutyl)-3-pyridinecarboxamide,
N-(4-bromo-2,6-diethylphenyl)-4-chloro-2,6-dimethyl-5-propyl-3-pyridinecarboxamide,
N-(4-bromo-2,6-diethylphenyl)-4-chloro-2,5,6-trimethyl-3-pyridinecarboxamide,
5-allyl-4-chloro-N-(2,6-diethylphenyl)-2,6-dimethyl-3-pyridinecarboxamide,
5-allyl-4-chloro-N-(4-chloro-2,6-diethylphenyl)-2,6-dimethyl-3-pyridinecarboxamide,
5-allyl-4-chloro-N-(2,6-diethyl-4-methylphenyl)-2,6-dimethyl-3-pyridinecarboxamide,
5-allyl-4-chloro-N-(4-bromo-2,6-diethylphenyl)-2,6-dimethyl-3-pyridinecarboxamide,
4-chloro-N-(2,6-diethylphenyl)-2,6-dimethyl-5-(2-propynyl)-3-pyridinecarboxamide,
5-allyl-4-chloro-N-(4-chloro-2,6-diethylphenyl)-2,6-dimethyl-3-pyridinecarboxamide 1-oxide,
5-allyl-4-chloro-N-(2,6-diethyl-4-iodophenyl)-2,6-dimethyl-3-pyridinecarboxamide or
5-allyl-4-chloro-N-(2,6-diethyl-4-fluorophenyl)-2,6-dimethyl-3-pyridinecarboxamide.

11. A herbicidal composition comprising a compound of the formula 1:

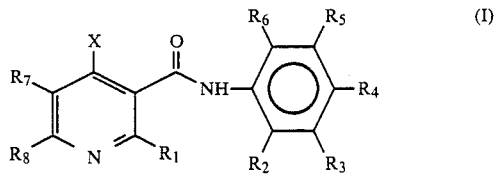

or 1-oxide or salt thereof, wherein $R_1$ is a $C_{1-11}$ alkyl group, a lower alkenyl group, a lower alkynyl group, a cycloalkyl group, a lower alkoxy-alkyl group, a lower alkylthioalkyl group, a phenyl group which can be unsubstituted or substituted by one or two groups selected from the group consisting of a halogen atom, a lower alkyl group and a lower alkoxy group, an aralkyl group whose nucleus can be unsubstituted or substituted by one or two groups selected from the group consisting of a halogen atom, a lower alkyl group and a lower alkoxy group, a haloalkyl group; $R_2$, $R_3$, $R_4$, $R_5$ and $R_6$ are the same or different and are selected from the group consisting of a hydrogen atom, a halogen atom, a cyano group, a nitro group, an amino group, a lower alkyl group, a lower haloalkyl group, a hydroxy group, a lower alkoxy group, an aryloxy group, a carboxy group or a lower alkoxycarbonyl group; $R_7$ is a hydrogen atom, a halogen atom, a lower alkyl group, a phenyl group which by unsubstituted or substituted by one or two groups selected from the group consisting of a halogen atom, a lower alkyl group and a lower alkoxy group, aralkyl group whose nucleus can be unsubstituted or substituted by one or two groups selected from the group consisting of a halogen atom, a lower alkyl group and a lower alkoxy group, a lower alkenyl group, a lower alkynyl group, a lower alkoxy group or a haloalkyl group; $R_8$ is a $C_{1-11}$ alkyl group, a lower alkenyl group, a lower alkynyl group, a cycloalkyl group, a lower alkoxyalkyl group, a lower alkylthioalkyl group, a phenyl group which can be unsubstituted or substituted by one or two groups selected from the group consisting of a halogen atom, a lower alkyl group and a lower alkoxy group, an aralkyl group whose nucleus can be unsubstituted or substituted by one or two groups selected from the group consisting of a halogen atom, a lower alkyl group and a lower alkoxy group, a haloalkyl group or $R_7$ and $R_8$ may be combined to form a group of $-CH_2)_m-$ (wherein m is 3 or 4); and X is a halogen atom and a carrier therefor.

12. A herbicidal composition according to claim 11 wherein X is a chlorine atom.

13. A herbicidal composition according to claim 11 wherein X is a bromine atom.

14. A herbicidal composition according to claim 11 wherein

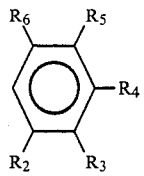

in the formula (I) is 2,6-diethylphenyl or 4-bromo-2,6-diethylphenyl.

15. A herbicidal composition according to claim 11 wherein

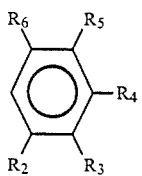

in the formula (I) is 4-chloro-2,6-diethylphenyl, 2,6-diethyl-4-methoxyphenyl or 2,6-diethyl-4-fluorophenyl.

16. A herbicidal composition according to claim 1 wherein $R_1$ and $R_8$ are methyl.

17. A herbicidal composition according to claim 1 wherein $R_7$ is ethyl, propyl, isobutyl, isopentyl, 2-butenyl, 3-butenyl, 2-methyl-2-propenyl, 3-methyl-2-butenyl, allyl or 2-propynyl.

18. A herbicidal composition of claim 11 wherein X is a fluorine atom.

19. A herbicidal composition of claim 11 wherein X is an iodine atom.

20. A herbicidal composition of claim 11 wherein the compound is:
4-chloro-5-ethyl-N-(2,6-diethylphenyl)-2,6-dimethyl-3-pyridinecarboxamide, 4-chloro-N-(2,6-diethylphenyl)-2,6-dimethyl-5-propyl-3-pyridinecarboxamide, 5-butyl-4-chloro-N-(2,6-diethylphenyl)-2,6-dimethyl-3-pyridinecarboxamide, 4-chloro-N-(2,6-diethylphenyl)-2,6-dimethyl-5-(2-methyl-propyl)-3-pyridinecarboxamide, 4-chloro-N-(2,6-diethylphenyl)-2,6-dimethyl-5-(3-methyl-propyl)-3-pyridinecarboxamide, 4-chloro-N-(2,6-diethylphenyl)-2,6-dimethyl-5-(3-methyl-butyl)-3-pyridinecarboxamide, N-(4-bromo-2,6-diethylphenyl)-4-chloro-2,6-dimethyl-5-propyl-3-pyridinecarboxamide, N-(4-bromo-2,6-diethylphenyl)-4-chloro-2,5,6-trimethyl-3-pyridinecarboxamide, 5-allyl-4-chloro-N-(2,6-diethylphenyl) 2,6-dimethyl-3-pyridinecarboxamide, 5-allyl-4-chloro-N-(4-chloro-2,6-diethylphenyl)-2,6-dimethyl-3-pyridinecarboxamide, 5-allyl-4-chloro-N-(2,6-diethyl-4-methylphenyl)-2,6-dimethyl-3-pyridinecarboxamide, 5-allyl-4-chloro-N-(4-bromo-2,6-diethylphenyl)-2,6-dimethyl-3-pyridinecarboxamide, 4-chloro-N-(2,6-diethylphenyl)-2,6-dimethyl-5-(2-propynyl)-3-pyridinecarboxamide, 5-allyl-4-chloro-N-(4-chloro-2,6-diethylphenyl)-2,6-dimethyl-3-pyridinecarboxamide 1-oxide, 5-allyl-4-chloro-N-(2,6-diethyl-4-iodophenyl)-2,6-dimethyl-3-pyridinecarboxamide or 5-allyl-4-chloro-N-(2,6-diethyl-4-fluorophenyl)-2,6-dimethyl-3-pyridinecarboxamide.

21. A herbicidal composition of claim 11 wherein X is a fluorine atom.

22. A herbicidal composition of claim 11 wherein X is an iodine atom.

23. A herbicidal composition of claim 11 wherein the compound is:
4-chloro-5-ethyl-N-(2,6-diethylphenyl)-2,6-dimethyl-3-pyridinecarboxamide, 4-chloro-N-(2,6-diethylphenyl)-2,6-dimethyl-5-propyl-3-pyridinecarboxamide, 5-butyl-4-chloro-N-(2,6-diethylphenyl)-2,6-dimethyl-3-pyridinecarboxamide, 4-chloro-N-(2,6-diethylphenyl)-2, 6-dimethyl-5-(2-methyl-propyl)-3-pyridinecarboxamide, 4-chloro-N-(2,6-diethylphenyl)-2,6-dimethyl-5-(3-methyl-propyl)-3-pyridinecarboxamide,4-chloro-N-(2,6-diethylphenyl)-2,6-dimethyl-5-(3-methyl-butyl)-3-pyridinecarboxamide, N-(4-bromo-2,6-diethylphenyl)-4-chloro-2,6-dimethyl-5-propyl-3-pyridinecarboxamide,N-(4-bromo-2,6-diethylphenyl)-4-chloro-2,5,6-trimethyl-3-pyridinecarboxamide, 5-allyl-4-chloro-N-(2,6-diethylphenyl)-2,6-dimethyl-3-pyridinecarboxamide, 5-allyl-4-chloro-N-(4-chloro-2,6-diethylphenyl)-2,6-dimethyl-3-pyridinecarboxamide, 5-allyl-4-chloro-N-(2,6-diethyl-4-methylphenyl)-2,6-dimethyl-3-pyridinecarboxamide, 5-allyl-4-chloro-N-(4-bromo-2,6-diethylphenyl)-2,6-dimethyl-3-pyridinecarboxamide,4-chloro-N-(2,6-diethylphenyl)-2,6-dimethyl-5-(2-propynl)-3-pyridinecarboxamide, 5-allyl-4-chloro-N-(4-chloro-2,6-diethylphenyl)-2,6-dimethyl-3-pyridinecarboxamide 1-oxide, 5-allyl-4-chloro-N-(2,6-diethyl-4-iodophenyl)-2,6-dimethyl-3-pyridinecarboxamide or 5-allyl-4- chloro-N-(2,6-diethyl-4-fluorophenyl)-2,6-dimethyl-3-pyridinecarboxamide.

24. A method of inhibiting the growth of a plant which comprises treating said plant with an effective amount of the herbicidal composition of claim 11.

25. The method of claim 24 wherein X is a chlorine atom.

26. The method of claim 24 wherein X is a bromine atom.

27. The method of claim 24 wherein

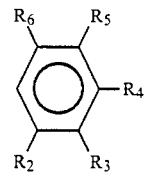

in the formula (I) is 2,6-diethylphenyl or 4-bromo-2,6-diethylphenyl.

28. The method of claim 24 wherein

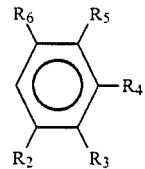

in the formula (I) is 4-chloro-2,6-diethylphenyl, 2,6-diethyl-4-methoxyphenyl or 2,6-diethyl-4-fluorophenyl.

29. The method of claim 24 wherein $R_1$ and $R_8$ are methyl.

30. The method of claim 24 wherein $R_7$ is ethyl, propyl, isobutyl, isopentyl, 2-butenyl, 3-butenyl, 2-methyl-2-propenyl, 3-methyl-2-butenyl, allyl or 2-propynyl.

* * * * *

UNITED STATES PATENT AND TRADEMARK OFFICE
CERTIFICATE OF CORRECTION

PATENT NO. : 4,978,385

DATED : December 18, 1990

INVENTOR(S) : HIROSHI YAGIHARA et al.

It is certified that error appears in the above-identified patent and that said Letters Patent is hereby corrected as shown below:

Column 1, line 12: change "Arts" to --Art--.

Column 1, line 53: change "publications" to --publication--.

Column 1, line 59: change "patent publications" to --Patent publications--.

Column 1, line 60: delete "the" before "formula".

Column 3, line 53: change "isophorore" to --isophorone--.

Column 3, line 60: add a comma --,-- after "esters".

Column 4, line 24: change "[" to --(--.

Column 5, line 6: add a comma --,-- after "examples".

Column 7, line 24: add --5- -- after "dimethyl-" and before "(2-propynyl)."

Column 7, line 65: change "chlropheryl" to --chlorophenyl--.

Column 8, line 7: change "methylphenyl" to --methoxyphenyl--.

Column 10, line 42: delete --4-chloro-N-(1-oxide---.

Column 10, line 43: change "4chloro" to --4-chloro--.

Column 10, line 55: change "iodcphenyl" to --iodophenyl--.

Col. 11, line 24: change "dimethyl3" to --dimethyl-3 --.

UNITED STATES PATENT AND TRADEMARK OFFICE
CERTIFICATE OF CORRECTION

PATENT NO. : 4,978,385                                    Page 2 of 2

DATED      : December 18, 1990

INVENTOR(S): Hiroshi Yagihara et al.

It is certified that error appears in the above-identified patent and that said Letters Patent is hereby corrected as shown below:

Column 11, line 26: change "dimethy13" to --dimethyl-3 --.

Column 12, line  7: add --the-- before "plant."

Column 12, line  9: change "of" before "'Evaluation'" to --labeled--.

Column 14, row 51: delete "f" from "166f".

Column 20, line 36: change "amine" to --amino--.

Col. 22, line 29: change "by" (1st occurrence) to --may be--.

Signed and Sealed this

Twentieth Day of April, 1993

Attest:

MICHAEL K. KIRK

Attesting Officer      Acting Commissioner of Patents and Trademarks